United States Patent
Kobida et al.

(10) Patent No.: US 9,884,143 B2
(45) Date of Patent: Feb. 6, 2018

(54) MEDICAL PERSONAL-SERVICES SUCTION HANDLE

(71) Applicant: Medline Industries, Inc., Mundelein, IL (US)

(72) Inventors: Michael Kobida, Barrington, IL (US); Michael Turturro, Chicago, IL (US)

(73) Assignee: Medline Industries, Inc., Northfield, IL (US)

( * ) Notice: Subject to any disclaimer, the term of this patent is extended or adjusted under 35 U.S.C. 154(b) by 469 days.

(21) Appl. No.: 14/291,876

(22) Filed: May 30, 2014

(65) Prior Publication Data
US 2015/0343121 A1  Dec. 3, 2015

(51) Int. Cl.
A61M 1/00 (2006.01)

(52) U.S. Cl.
CPC ........ A61M 1/0039 (2013.01); A61M 1/0047 (2013.01)

(58) Field of Classification Search
CPC .............. A61M 1/0039; A61M 1/0041; A61M 1/0031; A61M 1/0035; A61M 1/005; A61M 1/0058; A61M 1/0064; A61M 1/008; A61M 1/0084; A61M 1/0047; A61C 17/0202; A61C 17/0208; A61C 17/0217
See application file for complete search history.

(56) References Cited

U.S. PATENT DOCUMENTS

| 3,749,090 A | 7/1973 | Stewart |
| D279,924 S | 7/1985 | Osgood |
| D282,285 S | 1/1986 | Levy |
| D326,714 S | 6/1992 | Funakoshi |
| 5,203,769 A * | 4/1993 | Clement ............ A61B 18/1482 251/309 |
| D351,652 S | 10/1994 | Thompson |
| D357,064 S | 4/1995 | Barlett |

(Continued)

FOREIGN PATENT DOCUMENTS

WO  20081075241 A2  6/2008

OTHER PUBLICATIONS

Kimberly-Clark"KimVent" Oral Care q4 Kit & Individual Componets/Packs, Kimberly Clark, 2008, 6 pages.

(Continued)

*Primary Examiner* — Nathan R Price
*Assistant Examiner* — Melissa A Snyder
(74) *Attorney, Agent, or Firm* — Fitch, Even, Tabin & Flannery LLP

(57) ABSTRACT

A medical personal-services suction handle includes a hand-graspable housing and a primary suction pathway disposed through the hand-graspable housing and having a suction line port at one end and an intake port at an opposing end thereof. An on/off valve disposed at least partially within the primary suction pathway has a user-manipulable interface by which the on/off valve selectively opens the primary suction pathway and occludes the primary suction pathway. A user-engageable pneumatic pathway serves, when selectively engaged, to pneumatically couple the primary suction pathway to a secondary external port in the hand-graspable housing such that suction is applied via the primary suction pathway to both the intake port and the secondary external port. By one approach the secondary external port comprises a thumb-control port.

20 Claims, 8 Drawing Sheets

(56) References Cited

U.S. PATENT DOCUMENTS

| | | | |
|---|---|---|---|
| D387,862 S | 12/1997 | Mainiero | |
| 5,984,907 A | 11/1999 | McGee | |
| 6,129,547 A | 10/2000 | Cise | |
| 6,500,142 B1 | 12/2002 | Harreld | |
| 6,588,427 B1 | 7/2003 | Carlsen | |
| D483,475 S | 12/2003 | Kirwan | |
| D498,846 S | 11/2004 | Hayamizu | |
| D512,147 S | 11/2005 | Barker | |
| D518,175 S | 3/2006 | Hardin, Jr. | |
| D518,573 S | 4/2006 | French | |
| D535,393 S | 1/2007 | Pilvisto | |
| D545,439 S | 6/2007 | Draudt | |
| D564,093 S | 3/2008 | Marchand | |
| D571,458 S | 6/2008 | Kataoka | |
| D576,725 S | 9/2008 | Shumer | |
| D581,052 S | 11/2008 | Root | |
| D585,993 S | 2/2009 | Kousuge | |
| D606,651 S | 12/2009 | Bukoski | |
| 7,625,207 B2 * | 12/2009 | Hershey | A61C 1/16 433/100 |
| D622,842 S | 8/2010 | Benoist | |
| D630,728 S | 1/2011 | Dombrowski | |
| 7,866,477 B2 | 1/2011 | Sturm | |
| 7,867,190 B2 | 1/2011 | Ponsi | |
| D632,783 S | 2/2011 | Maesarapu | |
| D653,329 S | 1/2012 | Lee-Sepsick | |
| D669,578 S | 10/2012 | Burgess | |
| D678,512 S | 3/2013 | Bow | |
| D698,441 S | 1/2014 | Meguro | |
| D709,184 S | 7/2014 | Lee-Sepsick | |
| 8,764,731 B2 | 7/2014 | Burgess | |
| 8,834,407 B2 | 9/2014 | Greeson, Jr. | |
| D715,429 S | 10/2014 | Yu | |
| D718,437 S | 11/2014 | Osypka | |
| D718,445 S | 11/2014 | Yoshida | |
| D719,651 S | 12/2014 | Hoffmann | |
| 8,986,363 B2 | 3/2015 | McHugo | |
| 9,173,725 B2 | 11/2015 | Thorp | |
| D744,638 S | 12/2015 | Bow | |
| D749,717 S | 2/2016 | Kobida | |
| 9,248,228 B2 * | 2/2016 | Bono | A61M 3/0283 |
| 9,295,551 B2 | 3/2016 | Straubinger | |
| D753,291 S | 4/2016 | Ratjen | |
| D753,296 S | 4/2016 | Gill | |
| D753,823 S | 4/2016 | Hayamizu | |
| 9,314,356 B2 | 4/2016 | McHugo | |
| D756,517 S | 5/2016 | Sagalovich | |
| 9,332,973 B2 | 5/2016 | McWeeney | |
| 9,345,633 B2 | 5/2016 | Fuhr | |
| 2002/0103419 A1 | 8/2002 | Christopher | |
| 2004/0006380 A1 | 1/2004 | Buck | |
| 2008/0132760 A1 | 6/2008 | Takeuchi | |
| 2010/0240956 A1 | 9/2010 | Secrest | |
| 2011/0082431 A1 | 4/2011 | Burgess | |
| 2011/0098644 A1 | 4/2011 | Ponsi | |
| 2014/0207056 A1 | 7/2014 | Bono | |
| 2015/0258257 A1 | 9/2015 | Kidman | |
| 2015/0343121 A1 | 12/2015 | Kobida | |

OTHER PUBLICATIONS

Suzanne M. Pear, 'VAP Prevention: Critical Techniques and Tools.' Healthcare Purchasing News, May 2008, pp. 40-41.

* cited by examiner

MEDICAL PERSONAL-SERVICES SUCTION HANDLE

TECHNICAL FIELD

These teachings relate generally to suction handles and more particularly to medical personal-services suction handles.

BACKGROUND

The use of suction to complement or facilitate any of a variety of medical services and procedures is known in the art. The Yankauer suction tip, for example, is an oral suctioning tool used in medical procedures. The Yankauer suction tip is typically a firm plastic suction tip having a large opening surrounded by a bulbous head and is designed to allow effective suction without damaging surrounding tissue. This tool serves, for example, to suction oropharyngeal secretions in order to prevent aspiration. A Yankauer suction tip can also be used to clear operative sites during surgical procedures.

Suctioning tools often include a hand-graspable handle. So configured, the medical-services technician can firmly grip and manipulate the suctioning tool as desired. In some cases the handle includes an on-off switch to permit the technician to selectively fully open and fully close the suction pathway.

Some prior art suctioning-tool handles are also configured to work with a separate, additional component that can be selectively connected in-line with the pneumatic pathway of the handle. This separate component can have an external opening that pneumatically couples to the primary suctioning pathway. By partially occluding that external opening (for example, with a thumb) the technician can selectively vary the strength of the suction being applied via the suctioning tool. This capability can be useful when the technician seeks to apply only a modest, reduced amount of suction instead of the full suction being provided by the suction system.

Although useful, existing solutions in these regards are not necessarily wholly satisfactory to meet the needs of all application settings and all users. As one example in these regards, many suctioning tool handles are prepackaged with a separate thumb-port suction control component. In many cases, however, that ability to exert control over how much suction is being applied (rather than merely controlling the on-off suction state) is either unnecessary or unwanted by the technician. In those cases, it can represent a waste of material and resources to have included that separate thumb-port suction control component.

BRIEF DESCRIPTION OF THE DRAWINGS

The above needs are at least partially met through provision of the medical personal-services suction handle described in the following detailed description, particularly when studied in conjunction with the drawings, wherein.

Figure 1:
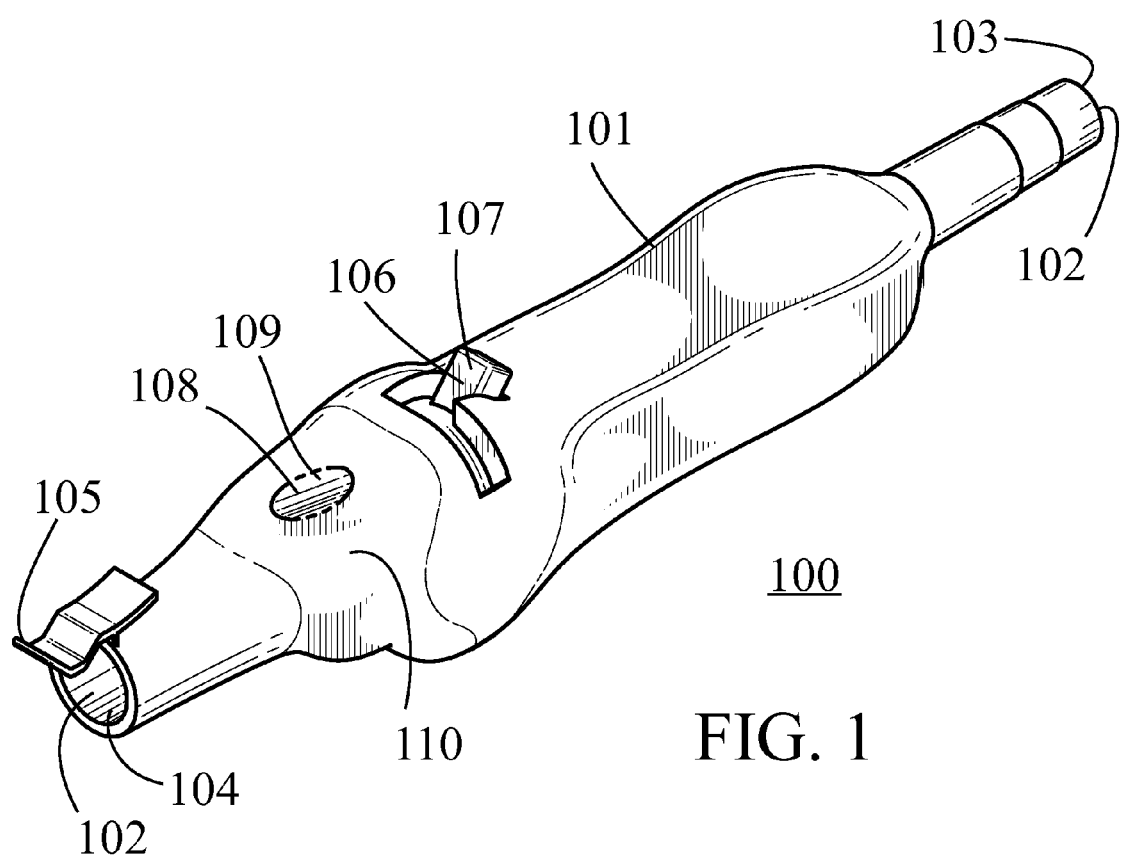
FIG. 1 comprises a perspective view as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, a medical personal-services suction handle includes a hand-graspable housing and a primary suction pathway disposed through the hand-graspable housing and having a suction line port at one end and an intake port at an opposing end thereof. An on/off valve disposed at least partially within the primary suction pathway has a user-manipulable interface by which the on/off valve selectively opens the primary suction pathway and occludes the primary suction pathway. A user-engageable pneumatic pathway serves, when selectively engaged, to pneumatically couple the primary suction pathway to a secondary external port in the hand-graspable housing such that suction is applied via the primary suction pathway to both the intake port and the secondary external port. By one approach the secondary external port comprises a thumb-control port.

By one approach the aforementioned on/off valve comprises a ball valve having a pneumatic pathway formed radially therethrough. The user-manipulable interface can comprise a tab that extends outwardly of the hand-graspable housing and that moves only within a corresponding slot that is formed in the hand-graspable housing. By one approach, that slot comprises an L-shaped slot. So configured, the on/off valve can be opened by moving the tab along a first portion of the L-shaped slot and the user-engageable pneumatic pathway can be selectively engaged by moving the tab along a second portion of the L-shaped slot.

So configured, such a handle can permit the user to conveniently select when to switch suction fully on and off while also permitting the user to decide when to use and exercise an ability to more finely control the suction strength via, for example, a thumb-control port. By one approach, these teachings avoid requiring the use of multiple separate components in order to provide variable suction control, thereby reducing both cost and set-up time.

By properly orienting the aforementioned L-shaped slot and the aforementioned tab, these teachings also provide a highly intuitive interface that clearly communicates to the user, both visually and haptically, the current suction state of the handle and the means by which that state can be selectively varied.

Figure 2:
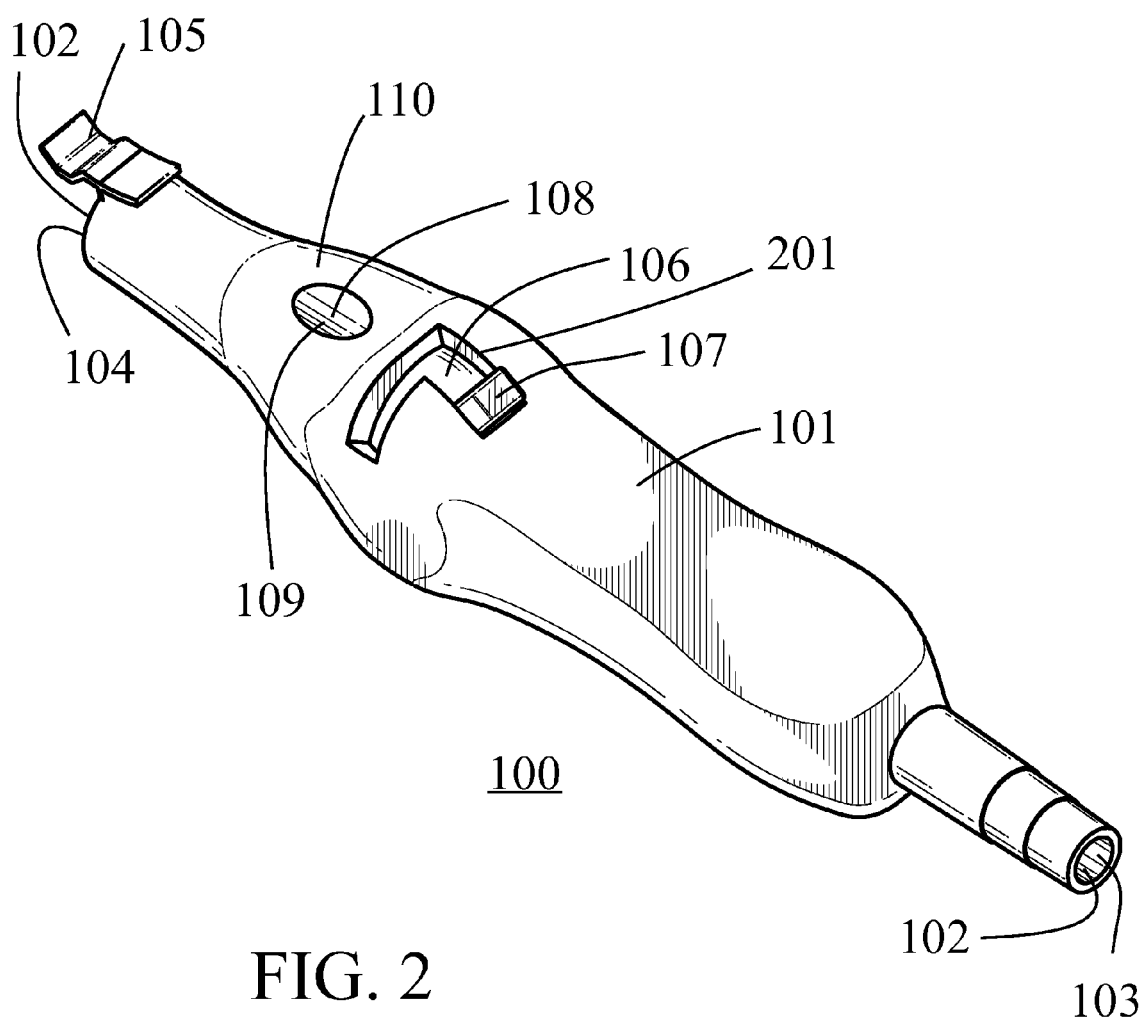
FIG. 2 comprises a perspective view as configured in accordance with various embodiments of these teachings.
Figure 3:
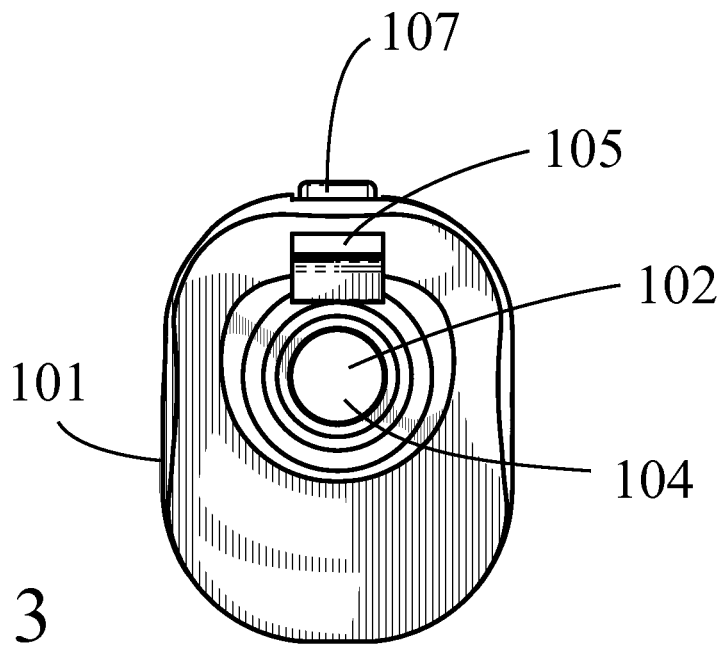
FIG. 3 comprises a front elevational view as configured in accordance with various embodiments of these teachings.

These and other benefits may become clearer upon making a thorough review and study of the following detailed description. Referring now to the drawings, and in particular to FIGS. 1-3, an in-line medical personal-services suction component 100 includes a hand-graspable housing 101 this hand-graspable housing 101 is sized and configured to be comfortably gripped by the average adult human hand. (As used herein, this reference to "personal" refers to the intended use of this apparatus with a given, individual patient. Accordingly, "personal" is not intended to specify that the apparatus be only used by a person for their own needs though, indeed, the term can include a person using the apparatus upon themselves as well as a medical services technician using the apparatus for that individual patient. Generally speaking, such apparatuses are used in conjunction with a single individual patient and are then disposed of.)

In this illustrative example the hand-graspable housing 101 is formed of plastic (using, for example, a molding process) but other materials can serve, in whole or in part, as desired. The exterior of the hand-graspable housing 101 can be as smooth or as textured as desired. By one approach the hand-graspable housing 101 comprises two halves that are joined together using any of a variety of connection methodologies including but not limited to clips, threaded members, snaps, adhesives, and sonic welding, to note but a few possibilities in these regards.

In this example the hand-graspable housing has a primary suction pathway 102 formed axially therethrough. In this example the primary suction pathway 102 has a circular cross-section and a constant diameter along its entire length but these teachings will accommodate other shapes if desired. This primary suction pathway 102 terminates at one end of the hand-graspable housing 101 as a suction line port 103 and at the opposite end of the hand-graspable housing 101 as an intake port 104.

So configured, the suction line port 103 can connect per ordinary prior art practice to a suction line to that connects to a source of suction such as a suction canister. Similarly, the intake port 104 can connect to any of a variety of suction-based tools including but not limited to a Yankauer suction tool. By one approach, if desired, a suction-based tool of choice, such as a Yankauer, can comprise an integral part of the hand-graspable housing 101 and hence can be integrally coupled to the intake port 104. Otherwise, and as illustrated here, a flexible clip 105 comprises a part of the intake port 104 and serves to temporarily secure a suction-tool of choice to the intake port 104. In this illustrative example the flexible clip 105 comprises an integral part of the hand-graspable housing 101.

As will be described in more detail below, the in-line medical personal-services suction component 100 has an on/off valve disposed therein at least partially within the primary suction pathway 102. This on/off valve includes or at least responds to a user-manipulable interface 106 by which the on/off valve selectively opens the primary suction pathway 102 and occludes the primary suction pathway 102 as desired. In this example the user-manipulable interface 106 includes a tab 107 that extends outwardly of the hand-graspable housing 101 and that moves only within a corresponding slot 201 that is formed in the hand-graspable housing 101.

Figure 4:
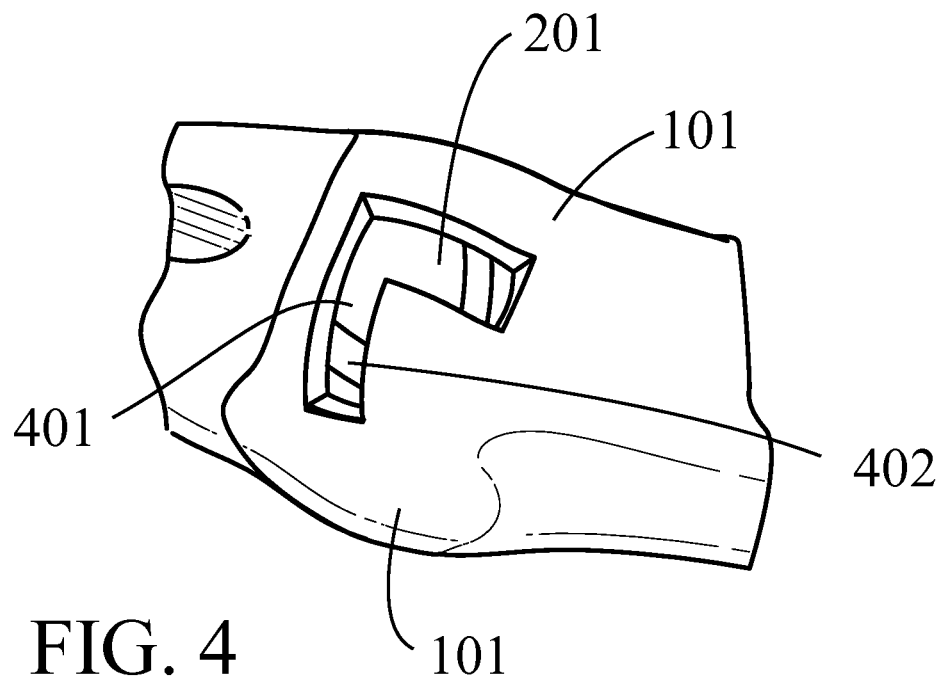
FIG. 4 comprises a perspective detail view as configured in accordance with various embodiments of these teachings.
Figure 5:
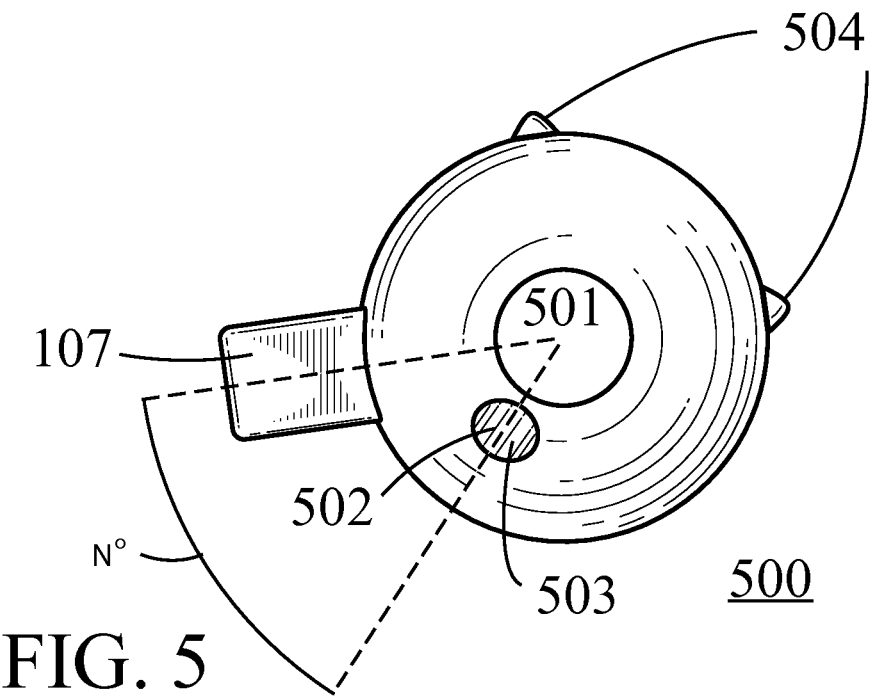
FIG. 5 comprises a plan view as configured in accordance with various embodiments of these teachings.
Figure 6:
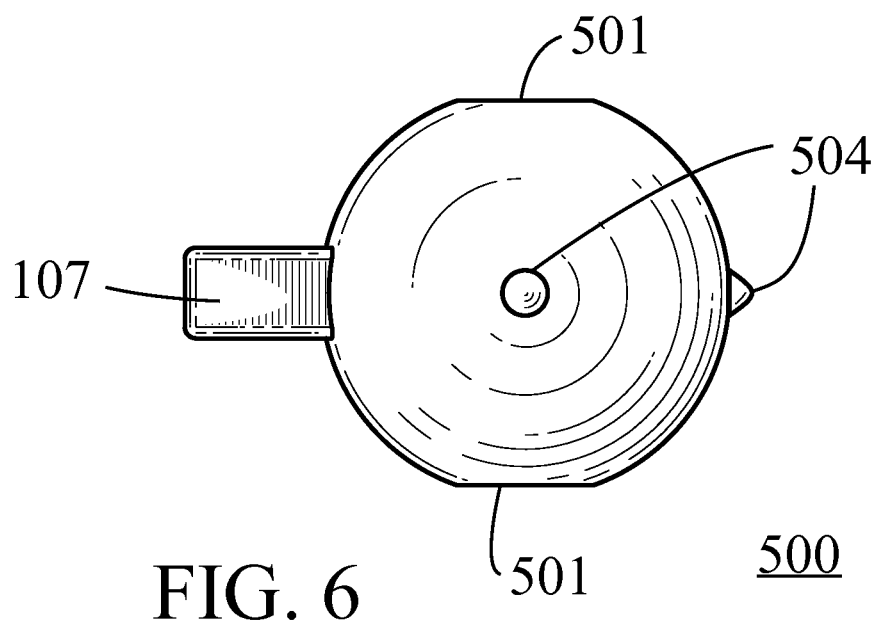
FIG. 6 comprises a side elevational view as configured in accordance with various embodiments of these teachings.
Figure 7:
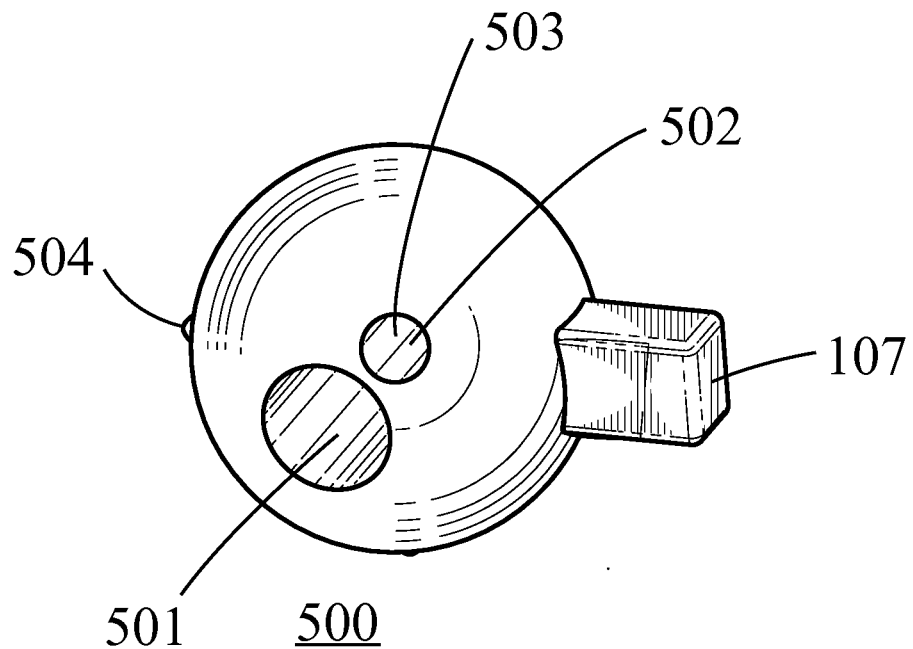
FIG. 7 comprises a perspective view as configured in accordance with various embodiments of the invention.
Figure 8:
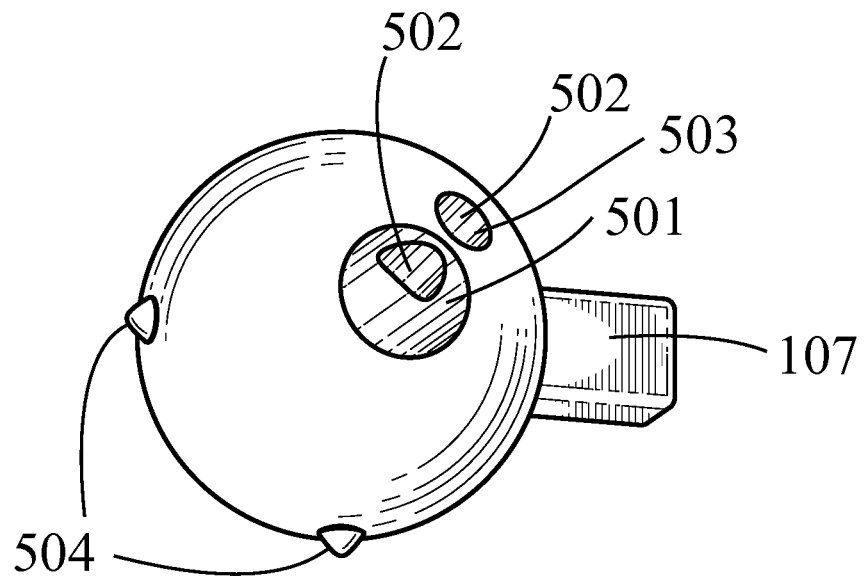
FIG. 8 comprises a perspective view as configured in accordance with various embodiments of these teachings.

Referring momentarily to FIG. 4, in this example the hand-graspable housing 101 includes an L-shaped slot 401 that is formed through a side wall thereof. This L-shaped slot 401 includes a first portion that comprises the aforementioned slot 201 that guides and constrains movement of the aforementioned tab 107 when moving the aforementioned on/off valve between a fully-off and a fully-on position. The L-shaped slot 401 also includes a second portion 402 to accommodate and guide lateral movement of the tab 107 from the fully-off position to a position that enables use of a user-engageable pneumatic pathway described further below.

Referring again to FIGS. 1 and 2, the hand-graspable housing 101 also includes a user-engageable pneumatic pathway configured here as a thumb-control port 108. This user-engageable pneumatic pathway, when selectively engaged (via the aforementioned tab 107 as described below) pneumatically couples the primary suction pathway 102 to a secondary external port 109 in the hand-graspable housing 101. In this illustrative example the thumb-control port 108 is disposed within a convex depression 110 that is formed in an exterior portion of the hand-graspable housing 101. This convex depression 110 helps to facilitate an ergonomic fit between the thumb-control port 108 and, for example, a user's thumb.

When engaged, suction applied via the primary suction pathway 102 is applied via the primary suction pathway to both the intake port 104 and the secondary external port 109. Accordingly, suction can be reduced at the intake port 104 when such is the case. Use of the thumb-control port 108 to vary the extent of this reduction is described below.

In this illustrative example the secondary external port 109 and the aforementioned slot 201 that comprises a first portion of the L-shaped slot 401 are axially aligned with one another. Other configurations and orientations are possible. Also in this illustrative example the secondary external port 109 and a part of the first portion of the L-shaped slot 401 that comprises the aforementioned slot 201 and that is closest to the secondary external port 109 are no further apart than 3 cm. Again, these teachings will readily accommodate other spacings as best suits the requirements and/or opportunities of a given application setting. For example, these features may be spaced no further apart than 4 cm, 5 cm, or even 6 cm if so desired.

As mentioned above, an on/off valve is disposed at least partially within the primary suction pathway 102 and serves to permit a user (via manipulation of the aforementioned tab 107) to selectively open and occlude that primary suction pathway 102. Referring now to FIGS. 5-8, by one approach that on/off valve comprises a ball valve 500. In this example, the ball valve 500 has a pneumatic pathway 501 formed radially therethrough. In this illustrative example this pneumatic pathway 501 has a same shape and cross-sectional diameter as the primary suction pathway 102. These teachings will accommodate other shapes and diameter sizes if desired.

Figure 9:
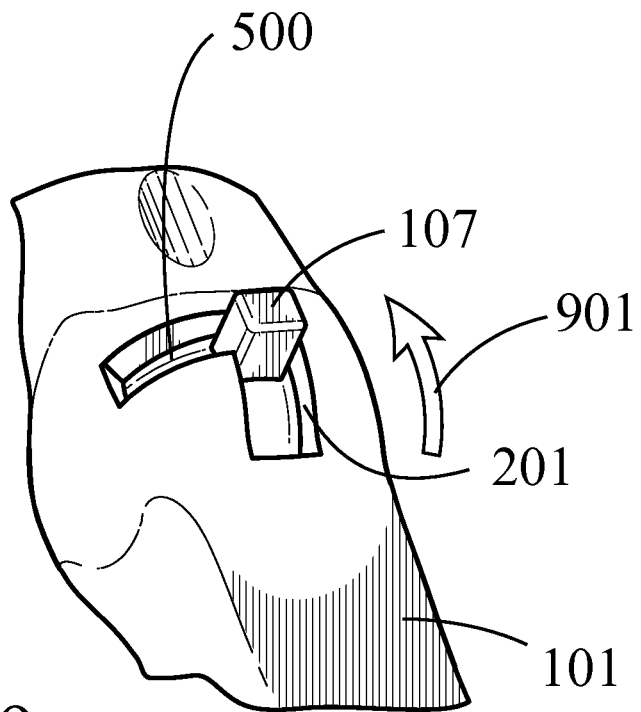
FIG. 9 comprises a perspective detail view as configured in accordance with various embodiments of the invention.

So configured, and referring momentarily to FIG. 1, when the tab 107 is disposed rearwardly as shown, the pneumatic pathway 501 in the ball valve 500 is completely nonaligned with the primary suction pathway 102. Accordingly, the body of the ball valve 500 occludes the primary suction pathway 102 and prevents air from being pulled into the primary suction pathway 102 via the intake port 104. Upon moving the tab 107 forward (as denoted by the arrow 901) along the first portion of the L-shaped slot 401 that comprises the above-mentioned slot 201 as shown in FIG. 9 the ball valve 500 rotates about its center and aligns its pneumatic pathway 501 with the primary suction pathway 102 to thereby pneumatically couple the suction line port 103 with the intake port 104 without obstruction. Accordingly, a user can selectively engage and disengage suction from the intake port 104 via this simple manipulation of the tab 107.

With continued reference to FIGS. 5-8, in this illustrative example the ball valve 500 also serves to selectively enable the aforementioned user-engageable pneumatic pathway by selectively pneumatically connecting and disconnecting the primary suction pathway 102 with the aforementioned secondary external port 109. In particular, the ball valve 500 includes a secondary suction pathway 502 that couples the pneumatic pathway 501 in the ball valve 500 to an exterior port 503 on the periphery of the ball valve 500. In this example this secondary suction pathway 502 comprises a linear pathway. Also in this illustrative example the secondary suction pathway 502 is offset from the tab 107 by N degrees (where N can vary with the specifics of the application setting).

Figure 10:
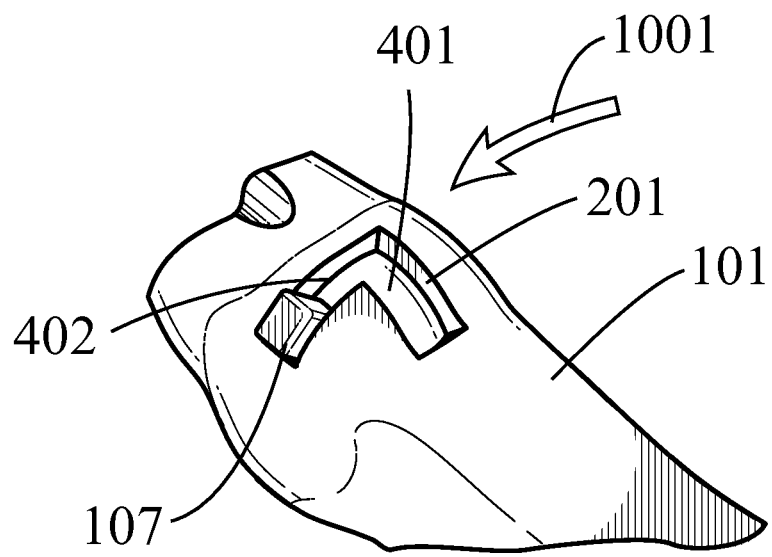
FIG. 10 comprises a perspective detail view as configured in accordance with various embodiments of these teachings.

So configured, and referring now momentarily to FIG. 10, upon moving the tab 107 along the second portion 402 of the L-shaped slot 401 (as denoted by the arrow 1001), the aforementioned secondary suction pathway 502 of the ball valve 500 is moved into alignment with the secondary external port 109 such that suction applied via the primary suction pathway 102 of the hand-graspable housing 101 is now applied to both the intake port 104 and the secondary external port 109. This coupling, in turn, will of course result in a lessening of the suction at the intake port 104. The amount of this lessening will vary with the diameter of the secondary external port 109 and the diameter of the secondary suction pathway 502 in the ball valve 500.

In addition, the user can control to some extent the amount of the lessening of suction at the intake port 104 by using their thumb or finger (or some other object) to vary the size of the pneumatically-exposed opening of the secondary external port 109. In particular, by completely blocking the secondary external port 109 full suction at the intake port 104 can be achieved. By only partially occluding the secondary external port 109 the user can achieve reduced suction at the intake port 104 as desired, both in terms of the strength of the suction and the duration of the reduction.

By one approach the ball valve 500 can be comprised of a material (or can be covered, in whole or in part, by a material) such as a relatively soft, sticky material (such as silicone, Polytetrafluoroethylene (PTFE), or the like) such that the ball valve 500 reliably forms a good pneumatic seal with the interior surfaces of the hand-graspable housing 101 while also being lubricious enough to permit relatively easy rotation and manipulation of the ball valve 500 by the user. Such an approach can help to retain the tab 107 in a selected position in the L-shaped slot 401.

As shown in FIGS. 5-8, these teachings will also accommodate providing the ball valve 500 with one or more knobs 504 that can interact, for example, with detents (not shown) on the interior surface of the hand-graspable housing 101. By properly locating these knobs 504 and corresponding detents, the position of the ball valve 500 can again be maintained in specific orientations of interest. For example, the ball valve 500 can be urged to be retained in one or more of the positions shown in FIGS. 1, 9, and 10 as desired.

Figure 11:
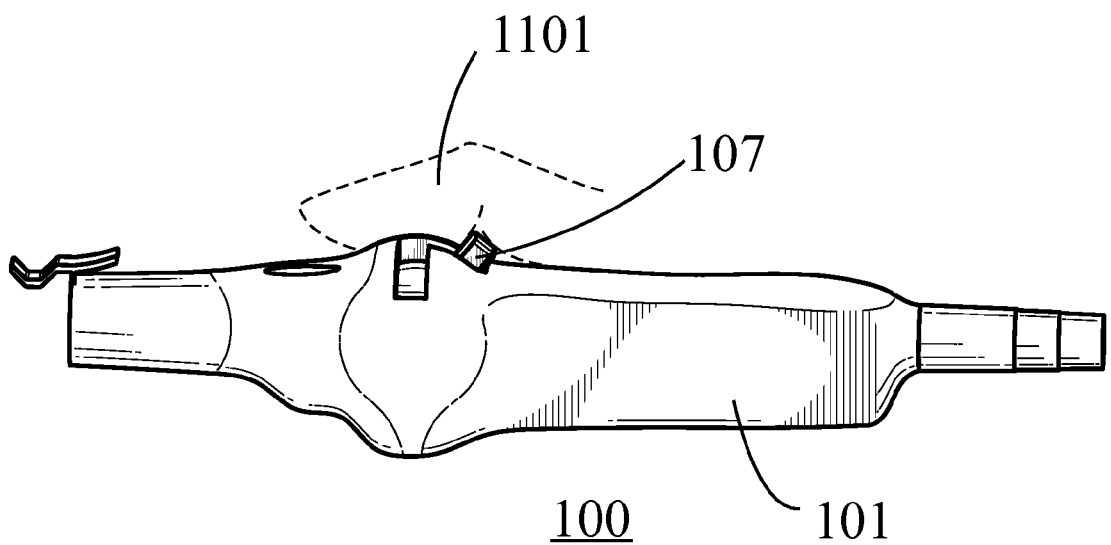
FIG. 11 comprises a side elevational view as configured in accordance with various embodiments of these teachings.
Figure 12:
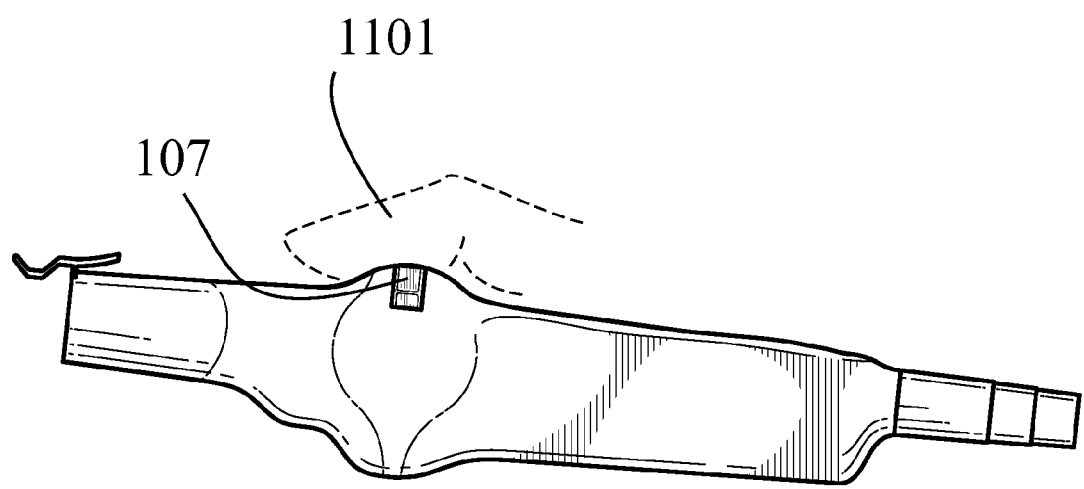
FIG. 12 comprises a side elevational view as configured in accordance with various embodiments of these teachings.

The particular configurations disclosed above offer a largely intuitive operating paradigm for the user. As one example, the linear alignment between the thumb-control port 108 and the tab 107 when moving the tab 107 from the suction-off position shown in FIG. 1 to the suction-on position shown in FIG. 9 causes the tab 107 to be readily sensed via a user's thumb 1101 as illustrated in FIG. 11 to thereby haptically indicate to the user that the thumb-control port 108 is not engaged and cannot serve to control the diminishment of suction at the intake port 104. Upon moving the tab 107 as shown in FIG. 10 to engage the operability of the thumb-control port 108, however, the tab 107 is moved to the side and will no longer engage the user's thumb 1101 (a configuration and condition illustrated in FIG. 12). Accordingly, and again, the user receives haptic information to signal to the user that the thumb-control port 108 is engaged and can be used to selectively lessen suction at the intake port 104.

Such an in-line medical personal-services suction component (whether used as a handle with detachable suction tools or as an integral part of a specific suction tool) can be inexpensively manufactured and can offer intuitive and reliable service. Such an apparatus will intuitively and easily permit a user to switch suction on and off without requiring the user to consider or control the thumb-control port if so desired. For users who wish to employ the thumb-control port, however, these teachings permit the thumb-control port to be easily and readily selectively rendered operable. Accordingly, all use cases are readily accommodated by this single apparatus.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A medical personal-services suction handle comprising:
   a hand-graspable housing;
   a primary suction pathway disposed through the hand-graspable housing and having a suction line port at one end and an intake port at an opposing end thereof;
   an on/off valve disposed at least partially within the primary suction pathway and having a user-manipulable interface by which the on/off valve selectively opens the primary suction pathway and occludes the primary suction pathway;
   a user-engageable pneumatic pathway;
   the on-off valve being further selectively switchable between an enabled and a non-enabled state and that, when selectively enabled, pneumatically couples the primary suction pathway to a secondary external port in the hand-graspable housing such that suction is applied via the primary suction pathway to both the intake port and the secondary external port and that, when selectively disabled, pneumatically closes the second suction pathway such that no suction is applied to the secondary external port.

2. The medical personal-services medical personal-services suction handle of claim 1 wherein the on/off valve that selectively opens the primary suction pathway and occludes the primary suction pathway comprises a ball valve having a pneumatic pathway formed radially therethrough.

3. The medical personal-services suction handle of claim 2 wherein the user-manipulable interface comprises a tab that extends outwardly of the hand-graspable housing and that moves only within a corresponding slot that is formed in the hand-graspable housing.

4. The medical personal-services suction handle of claim 2 wherein the user-engageable pneumatic pathway includes, at least in part, a pneumatic pathway formed through the ball valve.

5. A medical personal-services suction handle comprising:
a hand-graspable housing;
a primary suction pathway disposed through the hand-graspable housing and having a suction line port at one and an intake port at an opposing end thereof;
an on/off valve disposed at least partially within the primary suction pathway and having a user-manipulable interface by which the on/off valve selectively opens the primary suction pathway and occludes the primary suction pathway, wherein the on/off valve comprises a ball valve having a pneumatic pathway formed radially therethrough;
a user-engageable pneumatic pathway comprising a pneumatic pathway formed through the ball valve, wherein the user-engageable pneumatic pathway is selectively switchable between an enabled and a non-enabled state and that, when selectively enabled, pneumatically couples the primary suction pathway to a secondary external port in the hand-graspable housing such that suction is applied via the primary suction pathway to both the intake port and the secondary external port, and wherein the user-manipulable interface comprises a tab that extends outwardly of the hand-graspable housing and that moves only within a corresponding L-shaped slot that is formed in the hand-graspable housing, such that the on/off valve is opened by moving the tab along a first portion of the L-shaped slot and the user-engageable pneumatic pathway is selectively engaged by moving the tab along a second portion of the L-shaped slot.

6. The medical personal-services suction handle of claim 5 wherein the secondary external port comprises a thumb-control port.

7. The medical personal-services suction handle of claim 6 wherein the secondary external port and the first portion of the L-shaped slot are axially aligned with one another.

8. The medical personal-services suction handle of claim 7 wherein the secondary external port and a part of the first portion of the L-shaped slot that is closest to the secondary external port are no further apart than 3 cm.

9. The medical personal-services suction handle of claim 1 wherein the hand-graspable housing includes a clip disposed proximal to intake port to latch an intake to which the hand-graspable housing connects via the intake port.

10. The medical personal-services suction handle of claim 1 wherein the hand-graspable housing has a convex depression formed in an exterior portion of the hand-graspable housing that includes the secondary external port such that the secondary external port is located within the convex depression.

11. An in-line medical personal-services suction component comprising:
an in-line suction path housing having a primary suction pathway disposed therethrough;
a user-engageable pneumatic pathway that is selectively switchable between an enabled and a non-enabled state and that, when selectively enabled, pneumatically couples the primary suction pathway to a secondary external port in the in-line suction path housing such that suction is applied via the primary suction pathway to the secondary external port and that, when selectively disabled, pneumatically closes the second suction pathway such that no suction is applied to the secondary external port.

12. The in-line medical personal-services suction component of claim 11 wherein the secondary external port comprises a thumb-control port.

13. The in-line medical personal-services suction component of claim 11 further comprising a user-manipulable interface by which a user selectively engages the user-engageable pneumatic pathway to pneumatically couple the primary suction pathway to the secondary external port.

14. The in-line medical personal-services suction component of claim 13 wherein the user-manipulable interface comprises a tab that extends outwardly of the in-line suction path housing.

15. The in-line medical personal-services suction component of claim 11 wherein the in-line suction path housing comprises a medical personal-services suction handle.

16. The in-line medical personal-services suction component of claim 15 further comprising:
an on/off valve disposed at least partially within the primary suction pathway and having a user-manipulable interface by which the on/off valve selectively opens the primary suction pathway and occludes the primary suction pathway.

17. The in-line medical personal-services suction component of claim 16 wherein the on/off valve comprises a ball valve having a pneumatic pathway formed radially therethrough.

18. The in-line medical personal-services suction component of claim 17 wherein the user-manipulable interface comprises a tab that extends outwardly of the in-line suction path housing and that moves only within a corresponding slot that is formed in the in-line suction path housing.

19. The in-line medical personal-services suction component of claim 18 wherein the user-engageable pneumatic pathway includes, at least in part, a pneumatic pathway formed through the ball valve.

20. The in-line medical personal-services suction component of claim 19 wherein the slot comprises an L-shaped slot that is formed in the in-line suction path housing, such that the on/off valve is opened by moving the tab along a first portion of the L-shaped slot and the user-engageable pneumatic pathway is selectively engaged by moving the tab along a second portion of the L-shaped slot.

\* \* \* \* \*

UNITED STATES PATENT AND TRADEMARK OFFICE
CERTIFICATE OF CORRECTION

PATENT NO. : 9,884,143 B2  
APPLICATION NO. : 14/291876  
DATED : February 6, 2018  
INVENTOR(S) : Michael Kobida and Michael Turturro Page 1 of 1

It is certified that error appears in the above-identified patent and that said Letters Patent is hereby corrected as shown below:

On the Title Page  
    Column 2, In Other Publications, delete "Componets" and insert --Components--.

In the Claims  
    Column 6, Line 61, In Claim 2, after "personal-services" delete "medical personal-services".

Signed and Sealed this  
Nineteenth Day of June, 2018

Andrei Iancu  
*Director of the United States Patent and Trademark Office*